United States Patent
Seth et al.

(10) Patent No.: US 6,773,718 B2
(45) Date of Patent: Aug. 10, 2004

(54) OIL ABSORBENT WIPE WITH RAPID VISUAL INDICATION

(75) Inventors: Jayshree Seth, Woodbury, MN (US); Hiroto Katagiri, Tokyo (JP); Hiroshi Sakurai, Kanagawa (JP)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/001,094

(22) Filed: Nov. 15, 2001

(65) Prior Publication Data

US 2003/0091618 A1 May 15, 2003

(51) Int. Cl.$^7$ ................................................ A61F 13/00
(52) U.S. Cl. ........................ 424/443; 424/401; 424/402
(58) Field of Search ................................ 424/443, 402, 424/401

(56) References Cited

U.S. PATENT DOCUMENTS

| | | |
|---|---|---|
| 3,971,373 A | 7/1976 | Braun |
| 4,643,939 A | 2/1987 | Sugiyama et al. |
| 4,755,178 A | 7/1988 | Insley et al. |

FOREIGN PATENT DOCUMENTS

| | | |
|---|---|---|
| JP | 56-8606 | 1/1981 |
| JP | 4-045591 | 2/1992 |
| JP | 5-18392 | 1/1993 |
| JP | 6-319664 | 11/1994 |
| WO | WO99/29220 | 6/1999 |
| WO | WO 01/85001 | 11/2001 |
| WO | WO 01/97669 | 12/2001 |
| WO | WO 02/064871 | 8/2002 |
| WO | WO 02/100231 | 12/2002 |

OTHER PUBLICATIONS

Wente Van A., "Superfine Thermoplastic Fibers", *Industrial Engineering Chemistry*, vol. 48, p. 1342 et seq. (1956).
Wente et al., "Manufacture of Superfine Organic Fibers", Report No. 4364 of the Naval Research Laboratories, published May 25, 1954.

*Primary Examiner*—Shengjun Wang
(74) *Attorney, Agent, or Firm*—Gary L. Griswold; Robert W. Sprague; William J. Bond

(57) ABSTRACT

There is provided an oil absorbing wipe material suitable for wiping a users' skin or hair and a method for their manufacture. The wipes comprise at least an oil absorbing porous film-like substrate of a thermoplastic material. Generally, the wipe changes transparency or color (a change in L* of about 10 or more) when loaded with oil to provide an oil absorption indication functionality. The wipe is formed by (a) providing a porous film-like substrate of a thermoplastic material capable of absorbing facial or body oils and changing transparency or color, and (b) coating the porous substrate with oil, either continuously or in regions, wherein the oil coating is not sufficient to change the transparency or color of the substrate such that it loses its oil absorption indication functionality. This oil coating being of a nature such that the coated porous substrate has an increased oil absorption indicating functionality.

37 Claims, 1 Drawing Sheet

OIL ABSORBENT WIPE WITH RAPID VISUAL INDICATION

BACKGROUND OF THE INVENTION

This invention relates to oil absorbent skin wipe products. The invention particularly relates to oil absorbent skin wiping products with an oil absorption indication function.

A significant amount of oil continuously oozes out of the skin of the face, particularly the nose, cheek and forehead. To maintain cleanliness, reduce shine and to improve the spreadability of cosmetics and other skin products it is important to remove any excess surface oil or sebum. Soap and water work to some extent but there are always times when one is not able to wash. Dry methods of removing these facial oils include the use of thin oil absorbent wipe materials. Oil absorbing wipes for removing facial oil have been described in the art. These wipes generally must be thin, conformable and non-abrasive, considerations not relevant to industrial oil absorbent materials.

Conventional paper type wipes have been used to remove facial oil. For example, natural or synthetic papers using vegetable fibers, synthetic pulp or kenaf have been used. These oil absorbent papers however are often irritating to the skin due to the hard and stiff nature of the fibers. To improve their smoothness, these papers have been continuously calendered and/or coated with powders such as calcium carbonate and sizing agents. Calendering however is not necessarily permanent and surface fibers can reform into a rough surface unless substantial amounts of binder or sizing agents are used, which decrease oil absorption. Paper wipes are also poor indicators as to their effectiveness, as papers generally do not significantly change appearance when they have absorbed oil or sebum.

Improvements to oil absorbing papers are described in Japanese Kokai No. 4-45591 which teaches adhering porous spherical beads onto the surface of an oil absorbing paper so as to solve the problems caused by calendering or coating of paper with powders such as calcium carbonate powders. These beads also are used to allegedly increase the capacity of the papers to absorb sebum. Japanese Unexamined Patent Publication (Kokai) No. 6-319664 discloses a high-density oil absorbing paper produced by mixing (a) a pulp material containing vegetable fibers, as the main component with (b) an inorganic filler, followed by paper-making to form a paper with a basis weight of 0.7 g/cm$^2$ or more. However, the oil absorbing papers disclosed in these patent publications still have a limited capacity to absorb oil or sebum and little indicating function as there is little change in opacity or color in the paper when oil is absorbed. Difficulty in confirming oil removal means that users of the oil clearing paper can not evaluate if or how much sebum is removed from the users' face when using the oil absorbing paper such that makeup and the like can be applied with confidence.

An oil absorbing paper for sebum is also disclosed in Japanese Examined Patent Publication (Kokoku) No. 56-8606, or U.S. Pat. No. 4,643,939, which describes a cosmetic oil absorbing paper produced by mixing hemp fibers with 10 to 70% by weight of polyolefin resin fibers and making a paper with a basis weight of from 12 to 50 g/cm$^2$. This paper will allegedly clear upon absorption of oil but still requires conventional papermaking techniques and would be rough to the touch. Japanese Unexamined Utility Model Publication (Kokai) No. 5-18392, discloses an oil absorbing synthetic paper comprising an oil absorbing paper with a smooth surface coating of inorganic or organic powder material such as clay particles, silica fine-particles, and powdered fibers. These oil-absorbing papers allegedly have some oil indicating effect by clarifying the paper upon oil absorption thus confirming oil absorption. However, the powder coating lowers the oil absorption capacity for these papers and it is still difficult to attain a clear change in the appearance of this type of oil clearing paper after oil absorption.

Japanese Unexamined Patent Publication (Kokai) No. 9-335451 (WO99/29220) discloses an oil wipe made of a porous thermoplastic film. This oil absorbing wipe film has higher oil absorption capacity than the oil absorbing papers and is also superior in confirming removal of oil following wiping as compared to oil absorbing papers. It is believed that the reason for this good oil removal indicating functionality is that these porous thermoplastic films exhibit low light transmittance before oil absorption because of irregular reflection of light, but the light transmittance increases substantially after the micro-pores of the film are filled with oils producing a large change in the film's opacity or light transmittance, and therefore appearance. This change in opacity clearly confirms to the user the removal of oil or sebum from his or her skin. Further, unlike the paper products, these film based wipes are soft, comfortable, smooth and nonirritating to the skin.

It is an object of the invention provide an oil absorbing wipe having a rapid oil absorption indicating function, such as described in WO99/29220, which product is easy to manufacture.

BRIEF SUMMARY OF THE INVENTION

The invention is directed to oil absorbing wipe materials suitable for wiping a users' skin or hair and a method for their manufacture. The wipes comprise at least an oil absorbing porous film-like substrate of a thermoplastic material. Generally, the wipe changes transparency or color (a change in L* of about 10 or more) when loaded with oil to provide an oil absorption indication functionality. The wipe is formed by (a) providing a porous film-like substrate of a thermoplastic material capable of absorbing facial or body oils and changing transparency or color, and (b) coating the porous substrate with oil, either continuously or in regions, wherein the oil coating is not sufficient to change the transparency or color of the substrate such that it loses its oil absorption indication functionality. This oil coating being of a nature such that the coated porous substrate has an increased oil absorption indicating functionality.

BRIEF DESCRIPTION OF THE DRAWING

The invention may be more easily understood in reference to the drawing in which.

DETAILED DESCRIPTION

Figure 1:
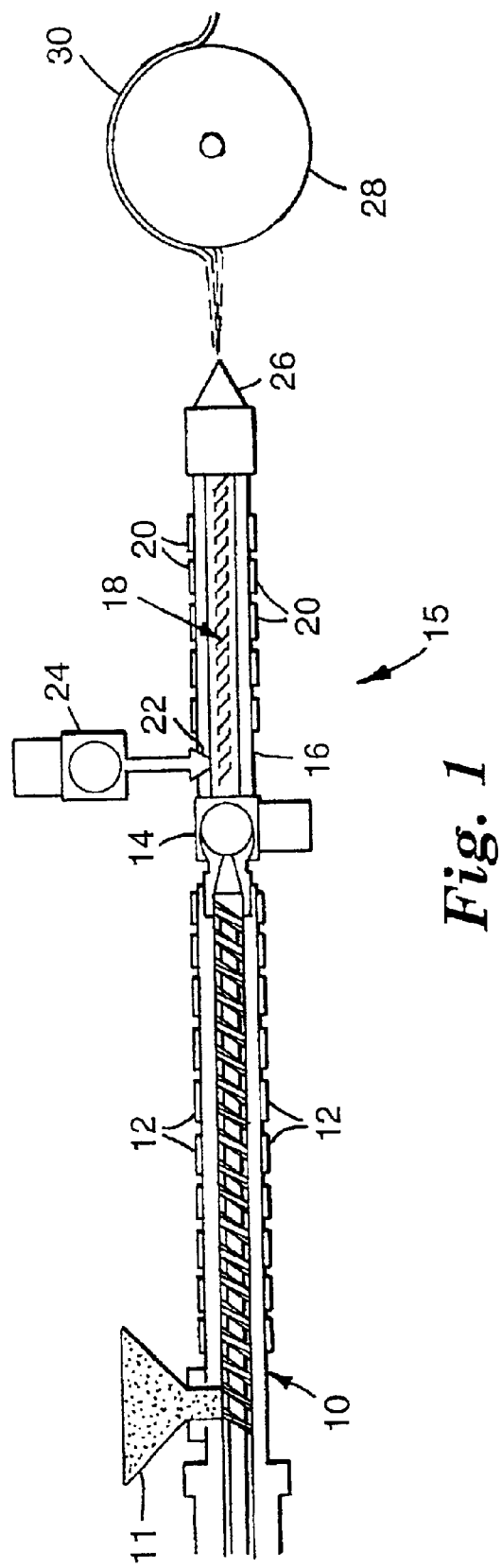
FIG. 1 is a schematic representation of apparatus for making a blown microfiber web for use in forming one embodiment of the present invention.

The individual oil absorbing wipes of the invention are generally coated with a nonvolatile organic, inorganic or synthetic oil or blends thereof. The oil coated areas can be continuous or discrete and fill at least partially, the porous structure of the thermoplastic wipe material. This oil coating increases oil indicating functionality of the wipe in the coated areas. The overall effect is that the oil coated areas change transparency or color more rapidly when used to remove facial oils or the like.

Many kinds of oils and fatty acid derivatives thereof are suitable. Preferred are vegetable based oils or, mineral oils or blends thereof. Examples of vegetable oils include but not limited to apricot kernel oil, avocado oil, baobab oil, black currant oil, Calendula officinalis oil, cannabis sativa oil, canola oil, chaulmoogra oil, coconut oil, corn oil, cottonseed oil, grape seed oil, hazel nut oil, hybrid sunflower oil, hydrogenated coconut oil, hydrogenated cottonseed oil, hydrogenated palm kernel oil, jojoba oil, kiwi seed oil, kukui nut oil, macadamia nut oil, mango seed oil, meadowfoam seed oil, mexican poppy oil, olive oil, palm kernel oil, partially hydrogenated soybean oil, peach kernel oil, peanut oil, pecan oil, pistachio nut oil, pumpkin seed oil, quinoa oil, rapeseed oil, rice bran oil, safflower oil, sasanqua oil, sea buckthorn oil, sesame oil, shea butter fruit oil, sisymbrium irio oil, soybean oil, sunflower seed oil, walnut oil, and wheat germ oil. Oils with vitamin-like qualities can be used such as, but not limited to, cod liver oil, shark liver oil, menhaden oil, mink oil, and palm oil. Oils with skin-protectant qualities can be used such as, but not limited to, carrot oil, echium plantagineum seed oil, and fomistopsis officinalis oil. Oils with skin-conditioning qualities can be used such as, but not limited to, borage seed oil, cohune oil, lesquerella fendleri oil, passionflower oil, passionfruit seed oil, and sweet almond oil. Oils with neutralizer qualities can be used such as, but not limited to, pine oil. Oils with moisturizer qualities can be used such as, but not limited to, aloe vera oil, babassu oil, brazil nut oil, camellia japonica oil, chia oil, ganoderma lucidum oil, hydrogenated castor oil, sweet cherry pit oil, and tea oil. Oils with emulsifier qualities can be used such as, but not limited to, neatsfoot oil, neem seed oil, PEG-5 hydrogenated castor oil, PEG-40 hydrogenated castor oil, PEG-20 hydrogenated castor oil isostearate, PEG-40 hydrogenated castor oil isostearate, PEG-40 hydrogenated castor oil laurate, PEG-50 hydrogenated castor oil laurate, PEG-5 hydrogenated castor oil triisostearate, PEG-20 hydrogenated castor oil triisostearate, PEG-40 hydrogenated castor oil triisostearate, PEG-50 hydrogenated castor oil triisostearate, PEG-40 jojoba oil, PEG-7 olive oil, PPG-3 hydrogenated castor oil, PPG-12-PEG-65 lanolin oil, hydrogenated mink oil, hydrogenated olive oil, lanolin oil, maleated soybean oil, musk rose oil, cashew nut oil, castor oil, dog rose hips oil, emu oil, evening primrose oil, and gold of pleasure oil. Oils with dispersant qualities can be used such as, but not limited to, PEG-5 castor oil, PEG-9 castor oil, PEG-15 castor oil, PEG-25 castor oil, PEG-36 castor oil, and PEG-18 castor oil dioleate. Oils having colorant qualities can be used such as, but not limited to, peppermint oil, spearmint oil, and zedoary oil. Oils having buffering qualities can be used such as, but not limited to, chamomile oil, and eucalyptus oil. Botanical oils can be used such as, but not limited to, balm mint oil. Oils with anti-microbial qualities can be used such as, but not limited to, tea tree oil. Oils with anti-oxidant qualities can be used such as, but not limited to, tocotrienols oil. Oils having fragrant qualities can be used such as, but not limited to, tangerine oil and lemongrass oil. Fatty acid derivatives of oils can be used such as, but not limited to, oleic acid, linoleic acid, and lauric acid. Substituted fatty acid derivatives of oils can be used such as, but not limited to, oleamide, propyl oleate and oleyl alcohol, provided that the volatility is not so high so as to evaporate before the product is used.

Nonlimiting examples of inorganic or synthetic oils include mineral oil, petrolatum, straight and branched chain hydrocarbons and derivatives thereof The individual oil absorbing wipes of the invention can also be provided with an embossing pattern. The embossed areas collapse, at least partially, the porous structure of the thermoplastic wipe material. This embossing increases the transparency of the wipe in the embossed areas. The overall effect is a visible pattern where the embossed areas are below the plane of the wipe face formed by the unembossed areas, for example 5 to $50\mu$ below the wipe outer face. This reduces the overall surface contact of a wipe relative to an overlying or underlying wipe in the package. This reduced surface contact between adjacent wipes increases the dispensability of the wipes in a package by decreasing the bond level between the wipes. This is particularly effective where the wipe is or rendered hydrophilic. The patterned embossing also reduces a wipe's rigidity, improving the texture and feel of the wipe. The embossing pattern's increased transparency also provides a visual reference as to what the wipe should appear like following oil absorption. The oil coating can be continuous and/or connected elements.

Alternatively, the oil coating could be a pattern of discrete elements such as dots, disconnected patterns or the like. The oil coating pattern can be formed by conventional techniques over from 1 to 100% of the surface area of the wipe, preferably 2 to 100% of the wipe surface area.

The oil absorbent wipe is a porous filmlike thermoplastic material; in a first preferred embodiment it is a porous stretched or oriented film made of a thermoplastic material; or alternatively in a second nonpreferred embodiment a consolidated porous thermoplastic microfiber nonwoven web which is filmlike. Filmlike as used herein is defined as thermoplastic films or consolidated nonwovens of thermoplastic fibers. The porous thermoplastic material can be coated on at least a portion of one face with an active agent. The wipe, whether used as is or with a coating, is preferably in a dry state, not wet, when used.

The porosity of the interstitial volume per unit area of the first preferred embodiment porous film material is preferably in the range of 0.0001–0.005 $cm^3$ as calculated by the equation:

Interstitial volume per unit area=[film thickness (cm)×1(cm)× 1(cm)×void content (%)]/100 (where the void content is the percentage of voids in the porous film).

The "void content" is more specifically defined as the percentage of an amount of filling material, when all of the voids of the porous film are filled with a material of the same composition as the film, with respect to a film with no corresponding voids. The void content of the porous film is preferably in the range of 5–50% and the thickness is preferably in the range of 5–200 $\mu$m.

The porous stretched film may be produced by various different methods using a thermoplastic material as the starting substance. In one preferred method, the film is produced by adding a filler to a transparent crystalline thermoplastic resin, forming a film using conventional methods such as blown extrusion or casting, and then stretching the film to create fine voids therein. A porous stretched thermoplastic film obtained in this manner has a large percentage of voids constituting the volume of the wipe compared to conventional paper oil cleaning wipes, and has excellent absorption of skin oils per unit area. Also, since the thermoplastic film has a structure with a uniform distribution of many fine voids, prior to wiping of skin oils from the skin surface it appears non-transparent due to light dispersion by the pore structures. However, after oil absorption the oils fill the voids or pores thus either preventing or reducing the degree of light dispersion. This together with the original opaque or transparent nature of the thermoplastic forming the film allows the oil absorbing effect to be clearly assessed by a change in transparency or opacity.

Examples of thermoplastic resins which can be used as the film forming material for production of the porous stretched thermoplastic film include, but are not limited to, polyethylene, polypropylene, polybutylene, poly-4-methylpentene and ethylene-propylene block copolymer.

Examples of preferred nonparticulate fillers that can be used in combination with the aforementioned thermoplastic resins to provide the fine voids include, but are not limited to, mineral oils, petroleum jelly, low molecular weight polyethylene, soft Carbowax and mixtures thereof. These nonparticulate fillers are preferred as they exhibit transparency upon absorption of oil. Mineral oils are preferred among these fillers because of their relatively low cost. However, additionally conventional particulate based fillers can also be used to form the porous film, such as talc, calcium carbonate, titanium dioxide, barium sulfate, etc.

The aforementioned fillers can be varied within a wide range within the starting thermoplastic resin used for production of the film. The amount of filler used is preferably in the range of 20–60% by weight, and more preferably 25–40% by weight of the starting thermoplastic material. If the amount of filler added to the starting material is under 20% by weight, the void content of the film resulting after stretching is reduced, thus lowering the amount of oil absorption, while if it is above 60% by weight it becomes more difficult to produce flexible coherent films.

Other additives may also be added as necessary in addition to the thermoplastic resin and filler in the production of the porous stretched thermoplastic film. For example, organic acids such as carboxylic acid, sulfonic acid and phosphonic acid, and organic alcohols. As additional suitable additives there may also be mentioned, for example, inorganic and organic pigment, aromatic agents, surfactants, antistatic agents, nucleating agents and the like. In a preferred embodiment, the wipe can be made hydrophilic by suitable melt additives or a coating or surface treatment.

The main starting materials and optional additives are melted and/or combined to form a film, producing a filler-containing thermoplastic film. The melting and mixing step (s) and the subsequent film forming step may be carried out according to known methods. An example of a suitable melt mixing method is kneading with a kneader, and examples of suitable film forming methods are the blown film method and the casting method. The blown film method, for example, can give tube-shaped films by melt mixing the main starting material, etc. and then blowing it up from a circular die. The casting method can give films by melt mixing the main starting material, etc. and then extruding it from a die onto a smooth or patterned chilled roll (cold roll). In a modified form of this casting method, the nonparticulate additives and/or fillers may be removed by washing off or extracting with a suitable solvent after extrusion of the melted mixture onto the chilled roll.

The formed thermoplastic film is then stretched to provide it with fine voids. As with the film forming, the stretching may also be carried out according to known methods, such as uniaxial stretching or biaxial stretching. For example, in the case of biaxial stretching, the stretching in the lengthwise direction may be accomplished by varying the speed of the driving roll, and the stretching in the widthwise direction may be accomplished by mechanical pulling in the widthwise direction while holding both ends of the film with clips or clamps.

The conditions for the film stretching are not particularly restricted, but the stretching is preferably carried out so as to give a void content in the range of 5–50% and a stretched film thickness in the range of 5–200 $\mu$m. If the void content upon stretching of the film is under 5% the amount of oil absorption will be reduced, while if it is over 50% the amount of oil absorption will be too great, making it difficult to clearly assess the oil absorbing effect. Also, if the film thickness is under 5 $\mu$m the amount of oil absorption capacity will be too low and the film will tend to adhere to the face making it more difficult to handle, while if it is over 200 $\mu$m the amount of oil absorption capacity will be too great and the film may feel stiff and harsh against the user's skin.

The stretching ratio for the thermoplastic film is usually preferred to be in the range of 1.5 to 3.0. If the stretching ratio is under 1.5 it becomes difficult to achieve a sufficient void content for oil absorption, while if it is over 3.0 the void content could become too large, causing too much oil absorption.

The average size of the voids formed by stretching of the film is usually preferred to be in the range of 0.2 to 5 $\mu$m. If the void size is under 0.2 $\mu$m it becomes impossible to rapidly absorb enough skin oil to create a clear change in transparency, while if it is over 5 $\mu$m the amount of oil absorption needed to permit a visible change in transparency may be too great.

As mentioned above, the interstitial volume per unit area of the porous stretched thermoplastic film obtained by the stretching process described earlier is preferably in the range of 0.0001–0.005 $cm^3$ and more preferably in the range of 0.0002–0.001 $cm^3$, as calculated by the equation defined above. If the interstitial volume of the film is under 0.1001 $cm^3$ it becomes difficult for the user to hold the oil cleaning wipe, while if it is over 0.005 $cm^3$ the amount of oil absorption is too great, and it becomes difficult to clearly assess the oil absorbing effect.

The second embodiment of a thermoplastic filmlike porous wipe in the invention is a consolidated web formed of thermoplastic microfibers. A representative apparatus useful for preparing such a web or wipe product is shown schematically in FIG. 1. The apparatus consists of a conventional BMF production configuration as taught, for example, in van Wente, "Superfine Thermoplastic Fibers," Industrial Engineering Chemistry, Vol. 48, pages 1342 et sec (1956), or in Report No. 4364 of the Naval Research Laboratories, published May 25, 1954 entitled "Manufacture of Superfine Organic Fibers" by van Wente, A., Boone, C. D., and Fluharty, E. L. The configuration consists of an extruder 10 having a resin hopper 11 and a series of heating jackets 12 which heat the extruder barrel. The molten polyolefin resin exits from the extruder barrel into a pump 14 which permits improved control over the flow of the molten polymer through the downstream components of the apparatus. Upon exiting from the pump 14, the molten resin flows into mixing means 15 including a resin conveying tube 16 which contains a Kenix type static mixer 18. A series of heating jackets 20 control the temperature of the molten resin as it passes through the conveying tube 16. The mixing means 15 also includes an injection port 22 near the inlet end of the conveying tube that is connected to a high pressure metering pump 24 which enables surfactant to be injected into the molten polyolefin resin stream as it enters the static mixer 18. After exiting from the conveying tube 16, the molten resin is delivered through a BMF die 26 into a high velocity hot air stream which draws out and attenuates the molten resin into microfibers. The microfibers solidify and form a cohesive web 30 as they travel to a collector 28. The collector can be a flat screen, a drum, a cylinder or a finely perforated screen belt. From the collector 28, the web 30 is taken to a calender where the web is consolidated under pressure, preferably from 500 to 1600 Newtons per lineal centimeter. This consolidation is advantageously carried out by calendering in the nip between two generally smooth rolls (e.g., they contact each other over about 90 percent of their surface area or greater, preferably 99 percent or greater), having a Shore A durometer hardness of about 50 or more, although one roll preferably has a Shore A durometer hardness of less than about 95. The consolidated web can then be collected and subsequently converted into individual wipes. This method is particularly preferred in that it produces fine diameter fibers and can be directly formed into a web without the need for subsequent bonding processes. Further the chaotic fibrous stream produced by this method can easily incorporate discrete fibers or particles that are introduced into the fibrous stream prior to collection as a web, such as disclosed in U.S. Pat. No. 4,100,324. These added fibers or particles can become entangled in the fibrous matrix without the need for additional binders or bonding processes. These added fibers can be incorporated to add loft, abrasiveness or softness to the web. Where abrasiveness is desired, the added fibers are generally from 40 to 70 $\mu$m in diameter, whereas 1–30 $\mu$m diameter added fibers could be used where loft and/or softness is desired. The overall basis weight of this wipe product would generally be from 10 to 500 g/m$^2$.

The webs are formed of fiber-forming thermoplastic materials, which materials include, for example, polyolefins, such as polyethylene, polypropylene or polybutylene; polyesters, such as polyethylene terephthalate or polybutylene terephthalate; polyurethanes or polyamides such as nylon 6 or nylon 66. The microfibers have an average diameter of less than 10 micrometers, preferably with an average diameter of 7 micrometers or less. Smaller average fiber diameters may be obtained with smaller diameter orifices and/or by decreasing the polymer flow rate or by increasing gas withdrawal behind the collecter.

The oil absorbing wipes are formed from the consolidated film-like microfiber webs such that the wipe has a void volume of from 40 to 80 percent, preferably 45 to 75 percent and most preferably 50 to 70 percent. Where the void volume is greater than 70 percent it is difficult to obtain a rapid change in transparency or opacity as large amounts of oil are necessary to create this change, also the material becomes to compliant and difficult to handle. Where the void volume is less than 40%, the material becomes too stiff and has an insufficient capacity to absorb oil. The average pore size of the wipe is generally from 3–15 microns, preferably 3 to 12 microns and most preferably 4 to 8 microns. If the pore size is less than 3 microns, it is difficult to get the rapid oil absorption rate needed. Void volume and pore size generally can be decreased by higher consolidation conditions and/or decreasing the average fiber diameter or narrowing the range of fiber diameters. If the pore size is greater than 15 microns the ability to retain absorbed oil is lessened as is the rapid oil indicating function. Generally the void volume, basis weight and pore size should be provided to yield an oil absorption capacity of from 0.7 to 6 mg/cm$^2$, preferably 0.8 to 5 mg/cm$^2$ and most preferably 0.9 to 4 mg/cm$^2$. If the oil absorption is less than this then the capacity to absorb facial oil is insufficient for most users and when greater than these levels then the rapid oil absorption indicating function is adversely impacted for most users.

A preferred material for forming the web fibers is polypropylene wherein the desired initial and end opacity for a given wipe is controlled by the basis weight of the web forming the wipe material, the hardness of the calendering rolls, and the calendering (or consolidation) pressure and temperature. Generally, for polypropylene, a web or wipe basis weight of about 10 gm/M$^2$ to 40 gm/M$^2$ has been found suitable to provide an adequate initial transparency while allowing a change in transparency at a suitably low oil loading level with a relatively soft hand. Generally, the Hand of the wipe should be 8 grams or less, preferably 1–7 grams and most preferably 1–6 grams. The Hand, drape, or flexibility of the webs is determined using INDA Test IST 90.0-75 (R82) using a Thwing-Albert Handle-O-Meter with a 10 cm by 10 cm sample and a slot width of 1.0 cm. Generally, as drape or Hand measurements decrease the sample is more conformable. For polypropylene wipes, basis weights of greater than about 40 gm/M$^2$ are too stiff to be useful as a facial wipe. For fibers formed of other polymers or polymer blends under similar calendering conditions, different wipe basis weight ranges may be suitable depending on the oil absorbing properties and relative stiffness of the fibers forming the web.

Higher calendering temperatures and pressures have been found to have significant effects on the original transparency, pore size and void volume and also the resulting oil absorption capacity of the consolidated wipe. Higher calendering temperatures in particular significantly increase the original transparency, thus decreasing the oil-indicating value of the wipe. Under certain circumstances, it would be desirable to use chilled calendering rolls to counteract this effect. However, when a web is over-calendered (e.g., under too high a pressure and/or temperature), the web does not become more rigid, however, the oil indicating function and absorption capacity does decrease.

If the original opacity is inadequate to produce a significant enough change in opacity, opacifying agents such as silica, talc, calcium carbonate or other like inorganic powders can be used at low levels. Such powders could be coated on the surface of the wipes or incorporated into the web structures. Suitable methods for incorporating opacifying agents into the web include that taught in U.S. Pat. No. 3,971,373 where a stream of particles is entrained into two separate converging melt-blown microfiber streams prior to collection. Another method of incorporating particulates is taught in U.S. Pat. No. 4,755,178 where particles are introduced into an airstream that converges into a flow of melt-blown microfibers. Preferably, only a small amount of such opacifying agents are included as they have the tendency to detract from the wipe softness.

In addition to the above, other conventional web additives such as surfactants, colorants, and antistatic agents can be incorporated into the web by known methods.

The invention oil absorbent wipes are generally characterized by the ability to change from opaque to translucent after absorbing only a moderate amount of oil, such as would be present on a person's skin (e.g., from 0 to 8 mg/cm$^2$). The oil absorbent wipes are particularly useful as cosmetic wipes as after absorbing skin oil at the levels excreted from common sebaceous glands, they will turn translucent, thus indicating that the undesirable oil has been removed and that makeup or other skin treatments can be applied. The oil-indicating effect is provided by the oil absorbing wipe which generally changes in L* by about 10 or more units, with a relatively low level of oil loading (e.g., 6 mg/cm$^2$ or less). The oil absorbing wipe is generally used as a single layer of the porous filmlike material but could be laminated to fibrous web materials, or films or the like.

The invention oil absorbing wipes are generally provided in a dispensable package of oil absorbing wipes of a filmlike thermoplastic porous material. The individual wipes are in the package in a stacked arrangement. By stacked it is meant that a face of one wipe will be over all, or substantial portion of one face, in continuous contact with all, or a substantial portion of, a face on an adjacent wipe in the package. Generally, the package will contain at least 2 or more individual wipes, preferably 10 to 1000.

The individual discrete wipes can be of any suitable size, however, generally for most applications the wipes would have an overall surface area of from 10 to 100 cm$^2$, preferably from 20 to 50 cm$^2$. As such, the wipes would be of a size suitable for insertion in a package, which could easily be placed in the user's purse or pocket. The material forming the dispensable containers is generally not of importance and can be formed of suitable papers, plastics, paper film laminates and the like. The shape of the tissues is generally rectangular; however, other suitable shapes such as oval, circular or the like can be used.

The oil-absorbing wipes of the invention can contain or be coated with any suitable active or nonactive ingredients or agents. Additional ingredients can comprises a wide range of optional ingredients. Particularly useful are various active ingredients useful for delivering various benefits to the skin or hair during and after oil removal and cleansing.

The coating compositions can also comprise a safe and effective amount of one or more pharmaceutically-acceptable active or skin modifying ingredients thereof. The term "safe and effective amount" as used herein, means an amount of an active ingredient high enough to modify the conditions to be treated or to deliver the desired skin benefit, but low enough to avoid serious side effects, at a reasonable benefit to risk ratio within the scope of sound medical judgment. What is a safe and effective amount of the active ingredient will vary with the specific active ingredient, the ability of the active ingredient to penetrate through the skin, the age, health condition, and skin condition of the user, and other like factors.

The additional oils are coated onto the oil absorbing wipes by conventional coating techniques at a level which decreases the time required for the wipe to change transparency or color u0on being used but does not result in the wipe completely changing its transparency level (i.e., there is sufficient residual change available such that the wipe L* can change by 10 or more when used). Generally, this balance would occur with an oil coating level of from 1 to 5 grams/m$^2$, preferably 1 to 4 grams/m$^2$, however this would depend on the porosity of the porous substrate and its thickness. The oil could be coated by, for example, spray coating, dip coating, gravure coating, knife coating, roll coating, or the like.

Test Methods
Caliper & Basis Weight

A 10 cm by 10 cm sample was die cut from the coated films and weighed to the nearest 0.1 gram. Three replicates were measured and averaged. The thicknesses of the coated films were measured in inches using a TMI direct contact gauge. 3–5 measurements were taken and averaged and reported in microns.

Void Volume

The porosity of the webs expressed as a Void Volume was calculated from the caliper (cm) and basis weight (grams/cm$^2$) of the films and the density of polypropylene (0.91 grams/cm$^3$). Void Volume=$\{1-[(\text{Basis Weight}/0.91)/\text{Caliper}]\} \times (\text{Caliper} \times 100 \text{ cm}^2)$.

Oil Absorption Capacity

The oil absorption properties of the films were measured using the following procedure. A 10 cm by 10 cm sample was cut from the web and weighed to the nearest 0.001 gram. The sample was dipped into a pan filled with white mineral oil. The sample was removed from the pan after one minute. The excess oil on the surface of the sample was carefully wiped off using tissues. The sample was then weighed to the nearest 0.001 gram. 3 replicates were tested and averaged. The Oil Absorption Capacity was calculated by: $(D_1-D_O)/A$ (mg/cm 2), where $D_O$=initial sample weight (mg), $D_1$=sample weight after dipping (mg) and A=sample area (cm$^2$).

Color Change Time

The ability of the films of the invention to absorb oil and rapidly change color was determined by the following procedure. A 85 cm by 15 cm strip of film was submerged in a pan filled with mineral oil. The time required for the film to completely change color was measured by an observer using a stop watch and is reported in Table 1 in seconds.

Color

The ability of the films to indicate oil absorption to the user, as evidenced by clearing of the film, was measured using a color test. As the films absorb oil, the color or transparency of the films change. The color change was measured using a SZ-Σ80 Colorimeter (Nippon Denshoku Kogyo Co.). A five-layer stack of film was prepared using 9 cm by 6 cm strips of film. The stack was placed in the calorimeter and the color was measured using the chromaticity value (L*). The stack was then dipped into mineral oil. After allowing to stand for one minute, excess surface oil was carefully wiped off using tissues, and chromaticity was measured again. L*initial and L*treated are reported in Table 1.

COMPARATIVE EXAMPLE

A microprous film was prepared similar to that described in PCT application WO99/29220 Example 1, having the following composition: 5D45 polypropylene (55%, Union Carbide Co.), mineral oil (38.7%, white oil #31, Amoco Oil and Chemical Co.), ultramarine blue pigment concentrate (6%, 60S 1270—Penn Color), nucleating agent (0.1%, Millad 3988, Milliken) and 0.2% zinc stearate. The microporous film had a thickness of 32 microns and a void content of approximately 25%.

Example 1

The microporous film described above in the comparative example was coated on one side with a solution of 6% olive oil and 3% Span™ 20 (sorbitan monolaurate, Uniqema (ICI Surfactants) in isopropyl alcohol. A microgravure roll was used in a reverse kiss configuration to coat the solution onto the microporous film. The isopropyl alcohol was air dried resulting in an olive oil coating weight of 1.4 grams/m$^2$. The film thickness was 32 microns Example 2

The microporous film described above in the comparative example was coated on one side with a solution of 9% olive oil and 3% Span™ 20 (sorbitan monolaurate, Uniqema (ICI Surfactants) in isopropyl alcohol. A microgravure roll was used in a reverse kiss configuration to coat the solution onto the microporous film. The isopropyl alcohol was air dried resulting in an olive oil coating weight of 2.7 grams/M$^2$. The film thickness was 32 microns.

Example 3

The microporous film described above in the comparative example was coated on one side with a solution of 12% olive oil and 3% Span™ 20 (sorbitan monolaurate, Uniqema (ICI Surfactants) in isopropyl alcohol. A microgravure roll was used in a reverse kiss configuration to coat the solution onto the microporous film. The isopropyl alcohol was air dried resulting in an olive oil coating weight of 3.3 grams/M$^2$. The film thickness was 32 microns.

Table 1 below shows that by coating the microporous films with oil, the absorption capacity for facial oil can be lowered and, the Color Change Time can be shortened considerably, while maintaining a color change differential which provides the visual indication as indicted by the L* initial and treated values. The coated films have lower absorption capacity hence clear more rapidly which provides users with lower facial sebum levels a quick visual indication that facial sebum has been absorbed by the film.

TABLE 1

| Film | Oil Coating Weight (g/m²) | Void Volume (cm³/100 cm²) | Oil Abs. Capacity (mg/cm²) | Color Change Time (sec) | L* initial | L* treated |
|------|---------------------------|---------------------------|----------------------------|-------------------------|------------|------------|
| C1   | 0                         | 0.081                     | 0.75                       | 2.0                     | 76.4       | 62.6       |
| 1    | 1.4                       | 0.059                     | 0.53                       | 1.8                     | 71.2       | 59.3       |
| 2    | 2.7                       | 0.046                     | 0.39                       | 1.5                     | 68.1       | 56.3       |
| 3    | 3.3                       | 0.037                     | 0.32                       | 1.4                     | 66.5       | 54.8       |

We claim:

1. An oil absorbing wipe suitable for wiping a users skin or hair comprising an oil absorbing porous film-like substrate formed of a thermoplastic film or consolidated nonwoven web of a thermoplastic material which porous substrate changes color when loaded with oil by a change in the L* value of 10 units or more when loaded with oil at 6 mg/cm² or less, the porous substrate having an oil based coating on at least 1 percent of the wipe material surface area, wherein the oil based coating is a vegetable-based or mineral based oil or blends thereof.

2. The oil absorbing wipe of claim 1 wherein the oil based coating is a continuous coating.

3. The oil absorbing wipe of claim 1 wherein the oil based coating is a discontinuous coating.

4. The oil absorbing wipe of claim 1 wherein the oil based coating is a vegetable-based or mineral based oil or blends thereof.

5. The oil absorbing wipes of claim 4 wherein the oil coating is coated at a level of from 1 to 5 g/m².

6. The oil absorbing wipe of claim 4 wherein the oil coating is coated at level of from 1 to 4 g/m².

7. The oil absorbing wipe of claim 4 wherein the oil coating is a vegetable oil or blend.

8. The oil absorbing wipe of claim 4 wherein the wipe is provided in a package which package contains at least 2 wipes.

9. The oil absorbing wipes of claim 8 wherein the package contains at least 10 to 1000 wipes.

10. The oil absorbing wipes of claim 8 wherein the individual wipes are from 10 to 100 cm².

11. The oil absorbing wipe of claim 4 wherein the oil absorbing wipe comprises a porous stretched film made of a thermoplastic material.

12. The oil absorbing wipe of claim 11 wherein interstitial volume per unit area of said porous stretched film is in the range of 0.0001–0.005 cm³ as calculated by the following equation:

interstitial volume per unit area=[film thickness (cm)×1(cm)×void content (%)]/100 (where the void content is the percentage of voids in the porous film).

13. The oil absorbing wipe of claim 11 wherein the void content of said porous stretched film is in the range of 5–50% and the film thickness is in the range of 5–200 μm.

14. The oil absorbing wipe of claim 11 wherein the porous film comprises thermoplastic porous film containing from 20 to 60 percent filler.

15. The oil absorbing wipe of claim 14 wherein the porous film contains a non-particulate filler.

16. The oil absorbing wipe of claim 15 wherein the non-particulate filler is mineral oil.

17. The oil absorbing wipe of claim 11 wherein the porous film voids have an average size in the range of from 0.2 to 5.0 microns (μm).

18. The oil absorbing wipe of claim 12 wherein the interstitial volume per unit area is from 0.0002 to 0.001 cm³.

19. The oil absorbing wipe of claim 4 wherein the porous oil absorbing wipe comprises a consolidated melt-blown web of thermoplastic fibers.

20. The oil absorbing wipe of claim 19 wherein the wipe has a void volume of from 40 to 80 percent.

21. A method of forming an oil absorbing wipe suitable for a user's face or skin comprising providing an oil absorbing porous film-like substrate formed of a thermoplastic film or consolidated nonwoven web of a thermoplastic material which porous substrate changes transparency or color when loaded with oil, coating the porous substrate with an oil based coating on at least 1 percent of the wipe material surface area.

22. The method of forming an oil absorbing wipe of claim 21 wherein the oil based coating is a continuous coating.

23. The method of forming an oil absorbing wipe of claim 21 wherein the oil based coating is a discontinuous coating.

24. The method of forming an oil absorbing wipe of claim 21 wherein the oil based coating is a vegetable-based or synthetic based oil or blends thereof.

25. The method of forming an oil absorbing wipe of claim 23 wherein the oil coating is coated at a level of from 1 to 5 g/m².

26. The method of forming an oil absorbing wipe of claim 23 wherein the oil coating is coated at a level of from 1 to 4 g/m².

27. The method of forming an oil absorbing wipe of claim 23 wherein the oil coating is a vegetable oil or blend.

28. The method of forming an oil absorbing wipe of claim 23 wherein the oil absorbing wipe comprises a porous stretched film made of a thermoplastic material.

29. The method of forming an oil absorbing wipe of claim 28 wherein interstitial volume per unit area of said porous stretched film is in the range of 0.0001–0.005 cm³ as calculated by the following equation:

interstitial volume per unit area=[film thickness (cm)×1(cm)×void content (%)]/100 (where the void content is the percentage of voids in the porous film).

30. The method of forming an oil absorbing wipe of claim 28 wherein the void volume of said porous stretched film is in the range of 5–50% and the film thickness is in the range of 5–200 μm.

31. The method of forming an oil absorbing wipe of claim 28 wherein the porous film comprises thermoplastic porous film containing from 20 to 60 percent filler.

32. The method of forming an oil absorbing wipe of claim 31 wherein the porous film contains a non-particulate filler.

33. The method of forming an oil absorbing wipe of claim 32 wherein the non-particulate filler is mineral oil.

34. The method of forming an oil absorbing wipe of claim 28 wherein the porous film voids have an average size in the range of from 0.2 to 5.0 microns (μm).

35. The method of forming an oil absorbing wipe of claim 29 wherein the interstitial volume per unit area is from 0.0002 to 0.001 cm³.

36. The method of forming an oil absorbing wipe of claim 28 wherein the porous oil absorbing wipe comprises a consolidated melt-blown web of thermoplastic fibers.

37. The method of forming an oil absorbing wipe of claim 36 wherein the wipes have a void volume of from 40 to 80 percent.

* * * * *

UNITED STATES PATENT AND TRADEMARK OFFICE
CERTIFICATE OF CORRECTION

PATENT NO. : 6,773,718 B2
DATED : August 10, 2004
INVENTOR(S) : Seth, Jayshree

It is certified that error appears in the above-identified patent and that said Letters Patent is hereby corrected as shown below:

Column 3,
Line 65, after "thereof", please insert -- . --

Column 6,
Line 27, after "$cm^3$" please insert -- , --
Line 29, please delete "0.1001" and insert -- 0.001 --.

Column 10,
Line 3, please delete "mg/cm 2" and insert -- $mg/cm^2$ --.
Line 20, please delete "calorimeter" and insert -- Colorimeter --.
Line 33, please delete "60S 1270" and insert -- 60S1270 --.
Line 54, please delete "2.7 grams/$M^2$" and insert -- 2.7 grams/$m^2$ --.
Line 64, please delete "3.37 grams/$M^2$" and insert -- 3.3 grams/$m^2$ --.

Signed and Sealed this

Eighth Day of February, 2005

JON W. DUDAS
*Director of the United States Patent and Trademark Office*